United States Patent [19]

Burns

[11] Patent Number: 4,877,520
[45] Date of Patent: Oct. 31, 1989

[54] DEVICE FOR SEPARATING THE COMPONENTS OF A LIQUID SAMPLE HAVING HIGHER AND LOWER SPECIFIC GRAVITIES

[75] Inventor: James A. Burns, Elizabeth, N.J.

[73] Assignee: Becton, Dickinson and Company, Franklin Lakes, N.J.

[21] Appl. No.: 202,625

[22] Filed: Jun. 6, 1988

Related U.S. Application Data

[63] Continuation-in-part of Ser. No. 106,092, Oct. 10, 1987, Pat. No. 4,818,386.

[51] Int. Cl.$^4$ .................. B01D 17/038; B01D 21/26
[52] U.S. Cl. ................................ 210/94; 210/516; 210/518; 422/101
[58] Field of Search ............... 210/94, 515, 516, 518, 210/782, 789; 494/16; 422/101, 102

[56] References Cited

U.S. PATENT DOCUMENTS

| | | | |
|---|---|---|---|
| 3,852,194 | 12/1974 | Zine | 210/789 |
| 3,897,343 | 7/1975 | Ayres | 210/516 |
| 3,909,419 | 9/1975 | Ayres | 210/518 |
| 3,919,085 | 11/1975 | Ayres | 210/516 |
| 3,920,557 | 11/1975 | Ayres | 210/516 |
| 4,055,501 | 10/1977 | Cornell | 210/516 |
| 4,088,582 | 5/1978 | Murty et al. | 210/516 |
| 4,101,422 | 7/1978 | Lamont et al. | 210/516 |
| 4,202,769 | 5/1980 | Greenspan | 210/516 |

Primary Examiner—W. Gary Jones
Assistant Examiner—Mathew O. Savage
Attorney, Agent, or Firm—Robert P. Grindle

[57] ABSTRACT

A device is provided for separating the components of a liquid sample by centrifugation by dividing that portion of the sample having a higher specific gravity from that portion having a lower specific gravity, by utilizing a dual component assemby arranged to move in an evacuated container into the area adjacent the two portions of the sample under centrifugal force. The assembly includes a substantially rigid core component which nests within a cup-shaped elastomeric component having a built-in spring action, and which components interact with each other to provide alternating dual seals and open flow paths in response to different pressure differentials on each side thereof.

11 Claims, 3 Drawing Sheets

DEVICE FOR SEPARATING THE COMPONENTS OF A LIQUID SAMPLE HAVING HIGHER AND LOWER SPECIFIC GRAVITIES

BACKGROUND AND STATEMENT OF THE INVENTION

This application is a continuation-in-part of co-pending application Ser. No. 106,092, filed Oct. 10, 1987 now U.S. Pat. No. 4,818,386. This invention relates generally to a device which separates what is usually called the heavier and lighter fractions of a liquid sample. More particularly, this invention relates to devices or assemblies utilizing an evacuated tube placed under centrifugation wherein a liquid sample is placed in the tube, and subsequently the tube is subjected to centrifugal force in order to cause the heavier fraction (or the fraction having the higher specific gravity) to the closed end of the tube while the lighter fraction (or that fraction having a lower specific gravity) moves toward the open end of the tube.

Such arrangements utilize some sort of barrier for moving into the area adjacent the two phases of the sample being separated in order to maintain the components separated for subsequent examination of the individual components. The thrust of all of the devices developed for use in the environment discussed above is to provide a barrier which divides cleanly the heavier and lighter fractions of the sample being separated.

When taking blood samples for test purposes, for example, whole blood generally is drawn into an evacuated collection tube, and the tube is centrifuged to separate the blood into the relatively lighter phase or component, as discussed above which is serum or plasma, and a heavier cellular phase. A variety of mechanical devices have been utilized in the past including piston-type arrangements for moving freely in the liquid sample in the evacuated tube so that the piston arrangements subsequently come to rest in the divided area between the heavier and lighter phases. While these mechanical arrangements have proved useful in a limited sense, they have not been entirely successful because they do not provide the clean separation discussed above.

The material utilized generally at this time for providing the barrier or separation between the heavier and lighter phases or the components having the lower and higher specific gravities include various thixotropic gel materials or sealants such as those described in U.S. Pat. No. 3,852,194, which is a mixture of silicone and hydrophobic silicon dioxide powders. Another form of thixotropic gel is a polyester gel which is presently utilized for a great many serum and/or plasma separation tub devices on the market. That material is taught and claimed in U.S. Pat. No. 4,101,422 issued July 18, 1978.

However, the present polyester gel serum separation tube requires, for example, special manufacturing equipment to prepare the gel and to fill the tubes. Both processes require rigid controls. Moreover, the shelf-life of the product is limited in that globules are sometimes released from the gel mass or network. These globules have a specific gravity that is less than the separated serum and will float in the serum and can clog the measuring instruments, subsequently, during the clinical examination of the sample collected in the tube.

Moreover, while the gel is chemically inert to blood samples, if certain drugs are present in the blood sample when it is taken, there can be an adverse chemical reaction with the gel interface.

In the invention described and claimed in the above-noted co-pending application, a mechanical separator is utilized which is non-temperature dependent during storage and shipping, is more stable to radiation sterilization, and eliminates the need for a special transport tube which is required for gel separation devices as discussed above for improved barrier integrity during transportation. The arrangement utilizes a dual component mechanical assembly arranged to move in an evacuated tube under the action of centrifugal force in order to separate the two portions of the sample.

The assembly includes a substantially rigid core component which nests within a cup-shaped elastomer component. The solid component, under certain operating conditions, is movable within the cup-shaped component. The two components operate together, and complement each other under the differing pressure differentials which are inherent in serum separation tubes, to provide alternating dual seals and open flow paths in response to those pressure differentials. As such, the arrangement provides a much more precise division between the two portions being separated from the original sample introduced into the tube.

With this invention, a different form of dual component system is provided with a solid core configured to move within the elastomer component in such a way that the bottom surface of the core bears against the bottom surface of the cup-shaped elastomer component. The latter, in turn, is configured to have a higher degree of built-in spring action. The interaction of the two components, therefor, responds rapidly to centrifugal force for opening the seals between the two components. The entire assembly moves, therefor, rapidly to the desired position separating the lighter and heavier fractions of a sample under investigation.

Before describing this invention in more detail, it should be well to note that the dual component device of the invention herein has a conventional specific gravity range within between about 1.03 and 1.09, and more specifically within the range of between about 1.05 and 1.06 so that the device will come to rest under centrifugal force substantially at the border between the heavier and lighter phases of the sample under consideration.

In addition, the central core portion of the dual component device may be comprised of a substantially rigid moldable thermoplastic material such as polyvinyl chloride, polystyrene, polyethylene, polypropylene, polyesters, and mixtures thereof, with a limitation being that the material is inert to the sample introduced in the assembly of the invention so as not to interfere with any desired subsequent testing. The cup-shaped portion, in turn, may be comprised of any natural or synthetic elastomer or mixtures thereof, with, again, the limitation concerning being inert to the sample of interest. The stopper may be comprised of similar elastomer combinations.

While the invention is directed to evacuated tubes in order to facilitate introduction of blood samples from the vein of a patient, it will be understood that the container in accordance with this invention does not necessarily need to be evacuated.

Other objects and advantages of this invention will be apparent from the following description, the accompanying drawings, and the appended claims.

DETAILED DESCRIPTION OF THE INVENTION

Figure 1:
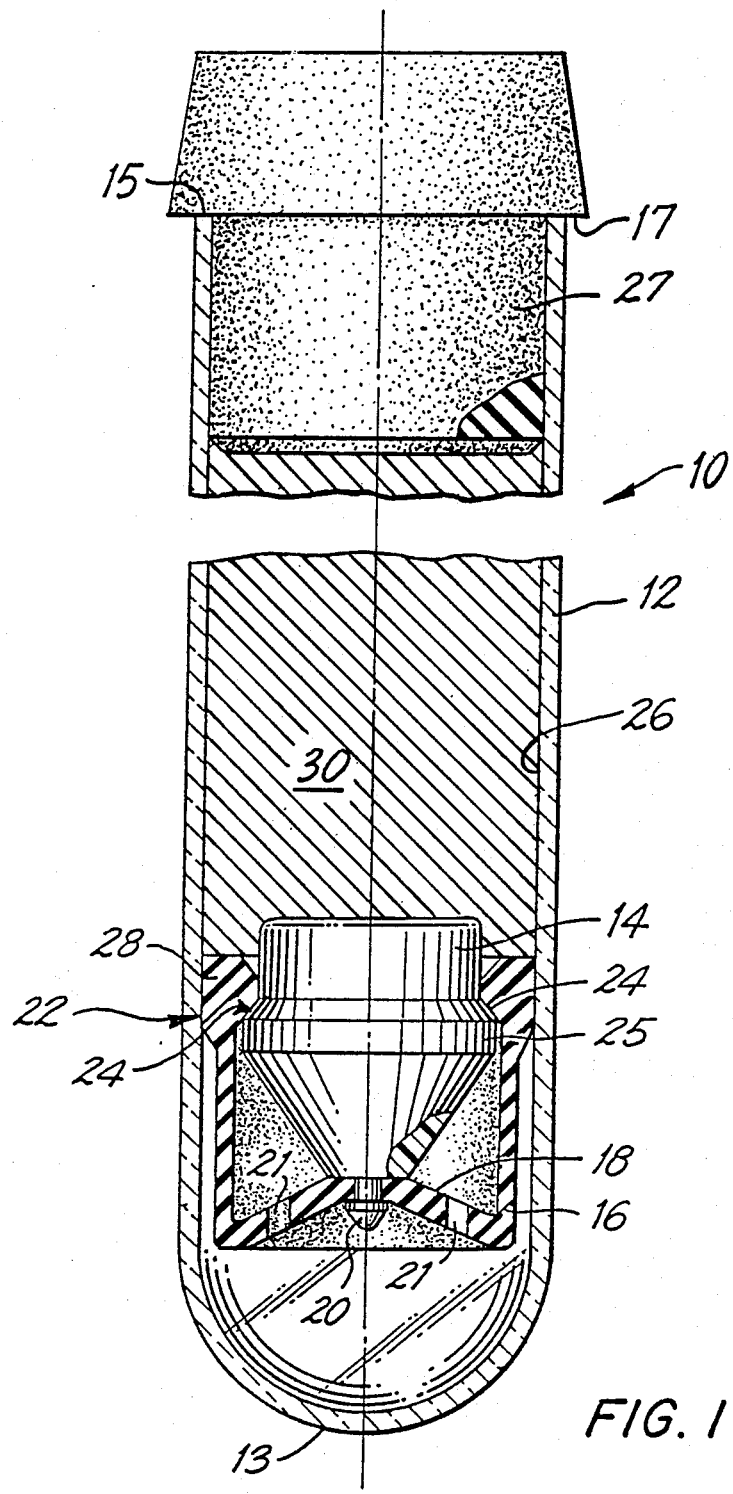
FIGS. 1-3 are longitudinal sectional views illustrating the device of the invention, and showing the various components thereof in different positions of movement sequentially during the use of the device of the invention.

Referring to the drawings in which like reference characters refer to like parts throughout the several views thereof, FIG. 1 illustrates the invention in the form of a serum separation tube having a closed end and an open end with the latter being arranged to be sealed by a cooperating stopper so as to maintain a vacuum in the tube once the stopper is in place.

In FIG. 1, the assembly of the invention generally designated 10 includes tube 12 having an open end 15 and a closed end 13. Tube 12 is transparent so that the user may readily observe what is going on with the contents thereof. Tube 12 may be plastic, but it is preferably glass.

Elastomeric stopper 27 is provided for insertion into the open end 15 of tube 12. Stopper 27 includes an upper annular portion and a lower annular portion of lesser diameter, with the lower portion being arranged to be inserted into tube 12 so that the internal surface 26 of tube 12 adheres to and seals against the external surface of the lower annular portion. Because of the differing diameters of the lower portion and the upper portion of stopper 27, an annular ledge or abutment 17 is arranged to seat on the top surface of open end 15 of tube 12 to further enhance the sealing between tube 12 and stopper 27. Tube 12 may be open at both ends (not shown) with a stopper 27 inserted in each end.

Further shown in FIG. 1 is a dual separator assembly, including a molded solid core 14 and an elastomeric cup-shaped flexible component 16. Solid core 14 nests in the cup-shaped elastomeric component 16. These two parts form dual seals 22 and 24. This is achieved by the annular ring portion 25 of solid core 14 cooperating with the upper annular ring portion 28 of the elastomeric cup-shaped component 16.

These dual sealing positions come about when the pressure above the dual component arrangement is different from the pressure below the dual component.

The improvement in the device of the invention here is the spring action in cup-shaped component 16. That is, bottom wall 18 thereof is raised as shown in FIG. 1 by its configuration. This causes solid core 14 to be raised through the snap connection 20 between core 14 and wall 18. Also, this spring action causes the upper annular ring portion 28 to flair outwardly. These movements and positioning effects the dual seals 22, 24.

Further as can be seen in FIG. 1, central core component 14 includes a snap connector 20, as discussed above, integral with central core component 14, which extends a bore in the bottom wall 18 of the elastomeric cup-shaped component 16. As can be seen in FIG. 1, the snap connector extends through the bore in wall 18 and spreads to hold the two parts together. Further in bottom wall 18 of component 16 is a plurality of apertures 21 providing flow communication around the dual separator assembly of the invention.

As can be seen in FIG. 1, a body fluid sample 30 has been introduced. Because of the pressure differential resulting above and below assembly 14, 16, the joint seals 22, 24 are in place.

Figure 2:
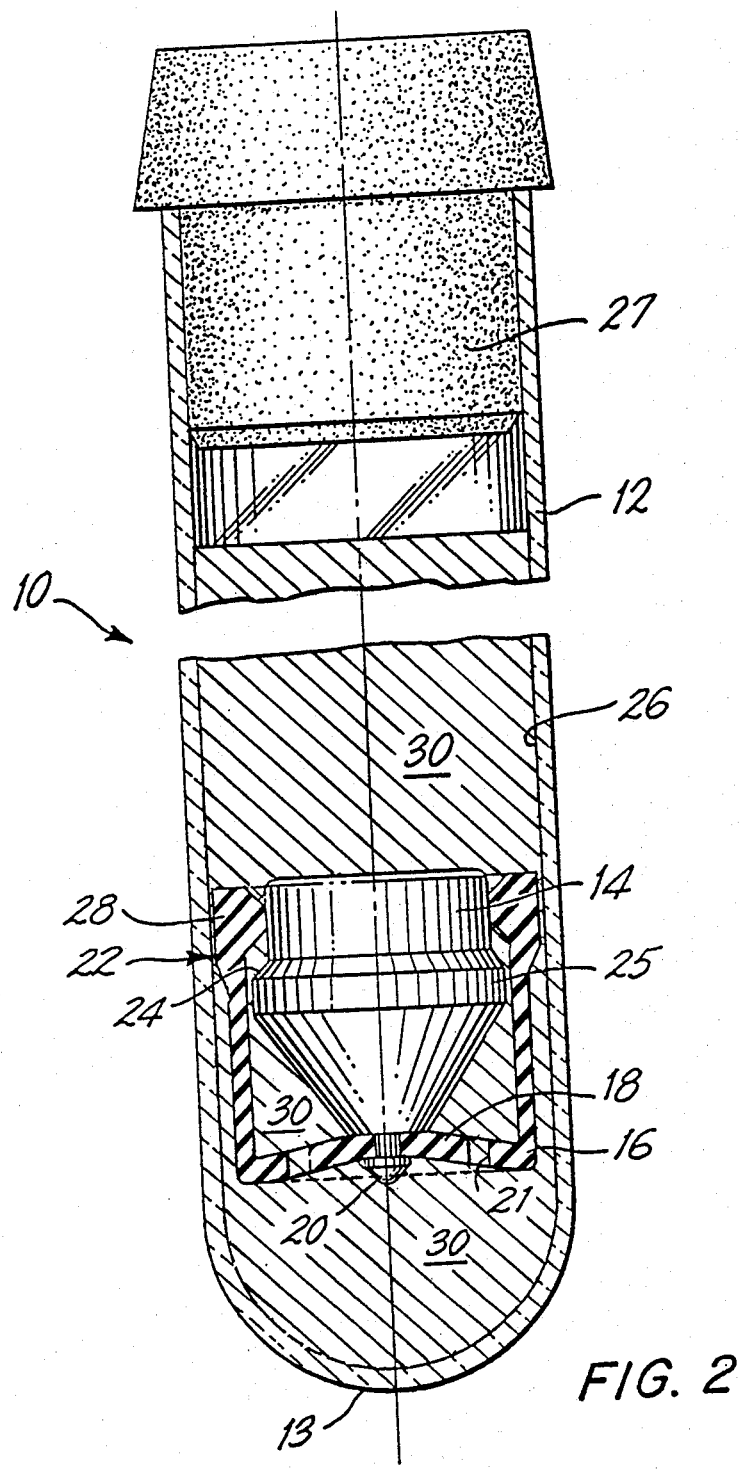

Then, as shown in FIG. 2, tube 12 is subjected to centrifugation. During centrifugation, the assembly 14, 16 is forced into the unsealed position. In this position, there is open passage between the area below assembly 14, 16 and the area above assembly 14, 16. As can be seen in FIG. 2, because of this equilibrium, a portion of sample 30 moves around and below assembly 14, 16. This happens because centrifugal force moves wall 18 downwardly, pulling core portion 14 away from the cooperating surface of annular portion 28 of the elastomeric cup-shaped portion of the assembly. This movement, in turn, opens seals, 22, 24.

Moreover, because the assembly has a specific gravity which is heavier than the serum and/or plasma or light phase of the sample being centrifuged in container 12, that portion 34 of the sample having a specific gravity heavier than the assembly 14, 16 moves below the assembly, while that portion 33 of the sample which is lighter than the specific gravity of assembly 14, 16 moves above the assembly. (FIG. 3) During centrifugation, the assembly 14, 16 itself moves to the interface between the heavier phase 34 and the lighter phase 33 of the initial sample 30 taken.

Figure 3:
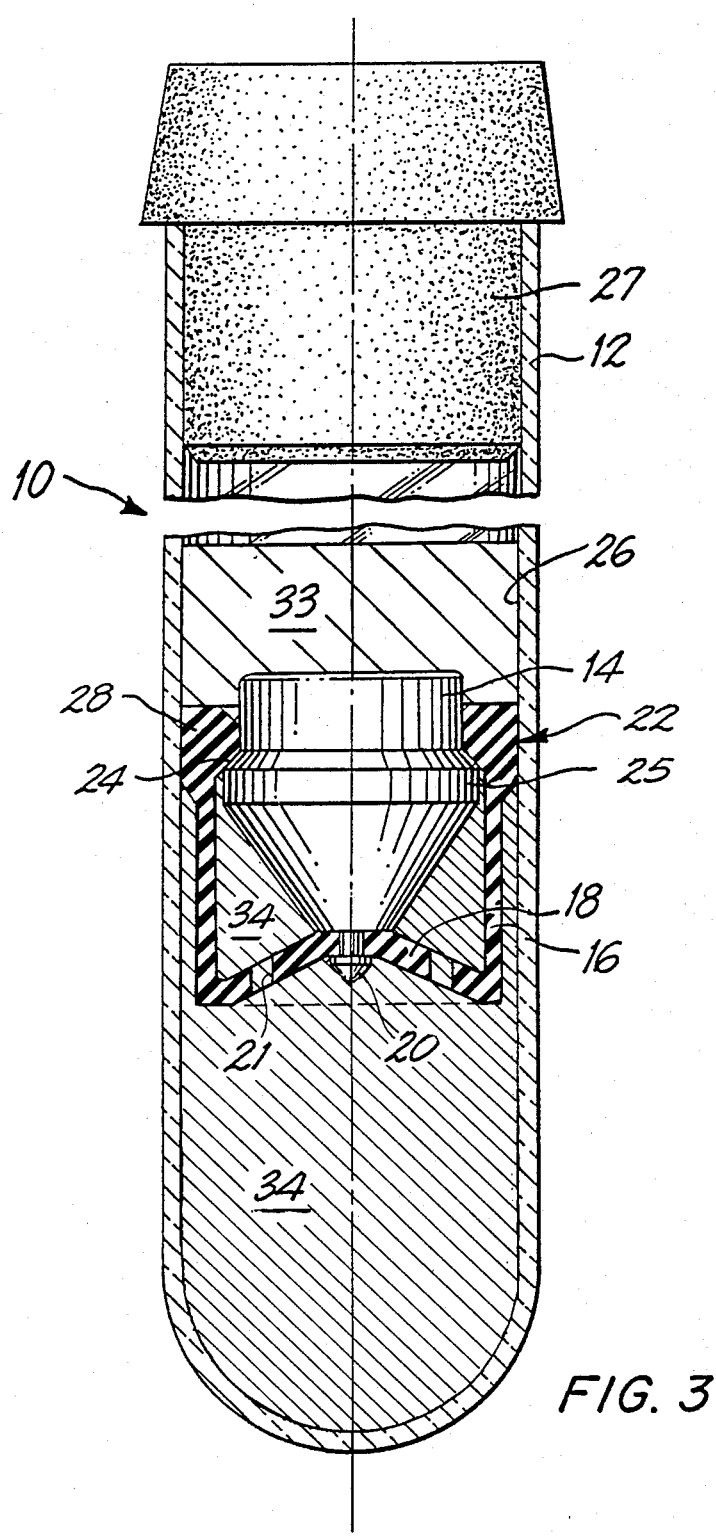

At this point, when centrifugation ends, wall 18 springs to the position shown in FIG. 3, and the dual seals 22, 24 move into place simultaneously with this movement of the assembly into its position at the interface, as discussed above. Because of this, a barrier is formed between the two phases.

Thus, as can be seen from the above, the invention provides a dual assembly arrangement for separating a liquid sample into the components thereof having a higher specific gravity and the components thereof having a lower specific gravity, or more specifically the serum/plasma phase and the cellular phase of a blood sample. The arrangement herein utilizes a unique dual arrangement of a solid core with a flexible cup-shaped diaphragm portion holding the solid core, and with the two parts interacting with each other in response to variations in pressure differential on each side thereof to form dual seals at appropriate times during use, and to provide flow passage around this dual assembly, at appropriate times to cause the appropriate separation of the two phases. In addition a spring action wall is employed as part of the flexible cup-shaped portion to initiate sealing and unsealing, and to improve upon the sealing function.

Also, because the arrangement herein is a mechanical arrangement as opposed to a gel, less rigid control is required in order to prepare and manufacture the device of the invention. Moreover, less procedures are required in order to produce a product, in accordance herewith, having an extended shelf-life, with the product being chemically inert to any chemicals in a sample introduced into the device. In addition, the device of the invention is substantially more stable in the environment of radiation sterilization, and is not temperature dependent during storage.

While the form of apparatus herein described constitutes a preferred embodiment of the invention, it is to be understood that the invention is not limited to this precise form of apparatus, and that changes may be made therein without departing from the scope of the invention which is defined in the appended claims.

What is claimed is:

1. Apparatus for separating the constituents in a liquid sample introduced into said apparatus into those constituents having a higher specific gravity from those constituents having a lower specific gravity under the action of centrifugal force, comprising
   (a) a tube-shaped transparent container having a closed end and an open end and defining a sample receiving chamber;
   (b) a stopper for closing said open end of said container; and
   (c) a dual barrier assembly movable axially in said container under the action of centrifugal force;
   (d) said dual barrier assembly having a specific gravity intermediate the specific gravity of constituents having a higher specific gravity and constituents having a lower specific gravity of a sample introduced into said container;
   (e) said dual barrier assembly providing selectively a dual annular seal and open passage therearound in response to pressure differentials in said container above and below said dual barrier assembly;
   (f) said dual barrier assembly comprising
      (1) a cup-shaped flexible portion;
      (2) said cup-shaped flexible portion having a first annular ring adjacent the upper edge thereof;
      (3) the outer circumferential edge of said first annular ring selectively movable into and out of sealing engagement with the internal wall of said container chamber in response to alternating equal and different pressures above and below said dual assembly;
      (4) means defining at least one opening in the bottom wall of said cup-shaped flexible portion providing flow communication therethrough;
      (5) a round solid core portion nested in said cup-shaped portion;
      (6) a second annular ring extending from the outer surface of said solid core portion;
      (7) said solid core portion movable vertical in said cup-shaped portion for causing said first and second ring to move into and out of sealing engagement with each other in response to alternating equal and different pressures above and below said dual assembly;
      (8) said bottom wall of said cup-shaped portion having a raised central section providing spring action responsive to pressure differentials on each side of said dual barrier assembly; and
      (9) means connecting said solid core portion and said raised central section of said bottom wall of said flexible cup-shaped portion.
2. The apparatus of claim 1 wherein
   (a) said container is evacuated.
3. The apparatus of claim 1 wherein
   (a) said container is glass.
4. The apparatus of claim 1 wherein
   (a) the specific gravity of said dual barrier assembly is within the range of between about 1.03 and 1.09.
5. The apparatus of claim 1 wherein
   (a) said stopper is needle penetrable for receiving a needle therethrough for introducing a sample into said sample receiving chamber.
6. The apparatus of claim 1 wherein
   (a) said core portion is formed from material selected from the group consisting of polyvinyl chloride, polyethylene, polypropylene, polystyrene, polyesters and mixtures thereof.
7. The apparatus of claim 1 wherein said cup-shaped portion is formed from material selected from the group consisting of natural elastomers, synthetic elastomers and mixtures thereof.
8. A dual barrier assembly for introduction into an evacuatable liquid collection tube, said assembly providing selectively, when inserted into an evacuatable liquid collection tube, a dual annular seal, and an open passage therearound in response to pressure differentials in a tube in which it is inserted, said assembly comprising
   (a) a cup-shaped flexible portion;
   (b) said cup-shaped flexible portion having a first annular ring adjacent the upper edge thereof;
   (c) the outer circumferential edge of said first annular ring selectively movable into and out of sealing engagement with the internal wall of a tube chamber into which said dual barrier assembly is inserted in response to alternating equal and different pressures above and below said dual barrier assembly;
   (d) means defining at least one opening in the bottom wall of said cup-shaped flexible portion providing flow communication therethrough;
   (e) a round solid core portion nested in said cup-shaped portion;
   (f) a second annular ring extending from the outer surface of said solid core portion;
   (g) said solid core portion movable vertically in said cup-shaped portion for causing said first and second ring to move into and out of sealing engagement with each other in response to alternating equal and different pressures above and below said dual barrier assembly;
   (h) said bottom wall of said cup-shaped portion having a raised central section providing spring action responsive to pressure differentials on each side of said dual barrier assembly; and
   (i) means connecting said solid core portion and said raised central section of said bottom wall of said flexible cup-shaped portion.
9. The apparatus of claim 8 wherein
   (a) the specific gravity of said dual barrier assembly is within the range of between about 1.03 and 1.09.
10. The apparatus of claim 8 wherein
    (a) said core portion is formed from material selected from the group consisting of polyvinyl chloride, polyethylene, polypropylene, polystyrene, polyesters and mixtures thereof.
11. The apparatus of claim 8 wherein said cup-shaped portion is formed from material selected from the group consisting of natural elastomers, synthetic elastomers and mixtures thereof.

* * * * *